Figure 1:
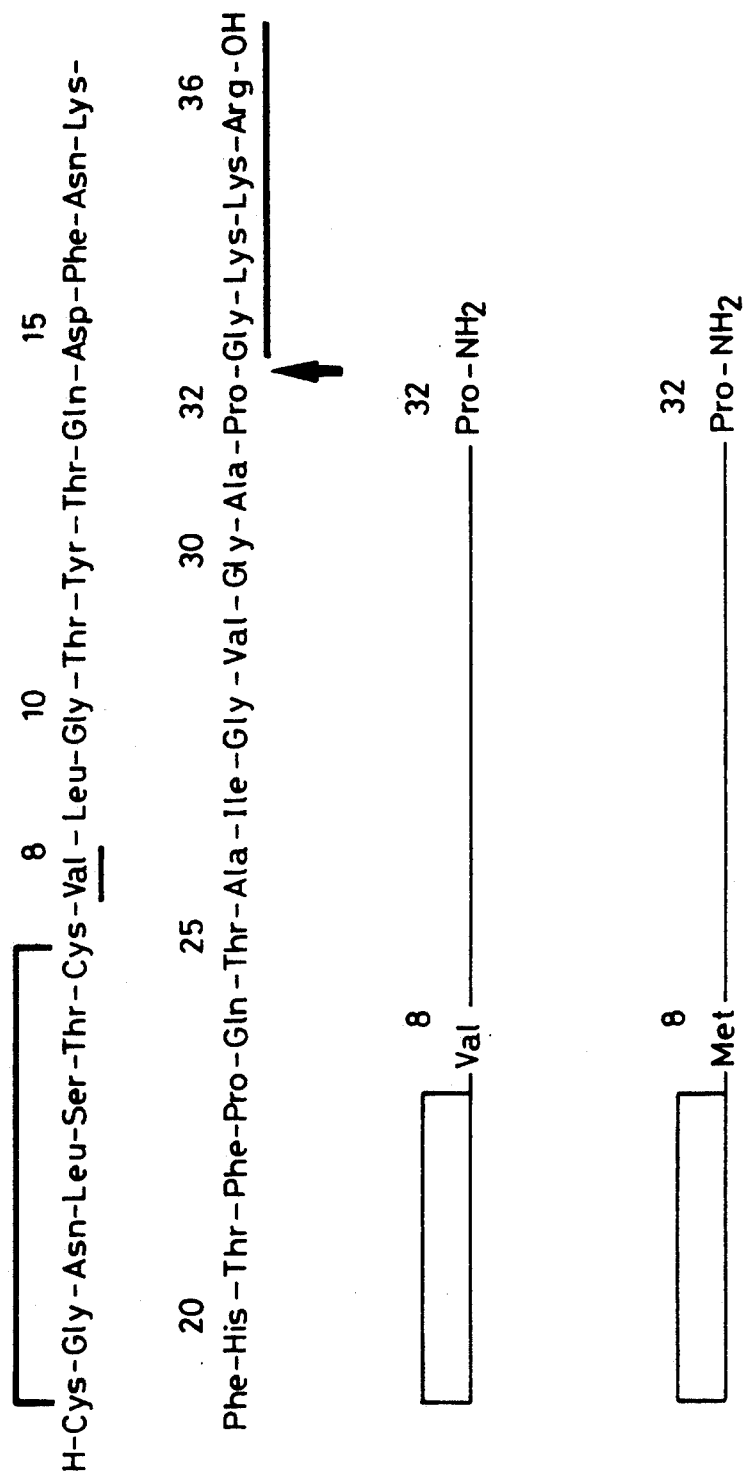

United States Patent [19]

Tanaka et al.

[11] Patent Number: 5,252,482
[45] Date of Patent: Oct. 12, 1993

[54] PRECURSOR OF A C-TERMINAL AMIDATED CALCITONIN

[75] Inventors: Shoji Tanaka; Kazuhiro Ohsuye; Ichiro Kubota; Norio Ohnuma, all of Osaka; Teruhisa Noguchi, Kanagawa, all of Japan

[73] Assignee: Suntory Limited, Osaka, Japan

[21] Appl. No.: 610,312

[22] Filed: Nov. 5, 1990

Related U.S. Application Data

[63] Continuation of Ser. No. 281,910, Dec. 7, 1988, abandoned, which is a continuation of Ser. No. 834,159, Feb. 27, 1986, abandoned, which is a continuation of Ser. No. 496,475, May 20, 1983, abandoned.

[30] Foreign Application Priority Data

May 20, 1982 [JP] Japan .................. 57-86181

[51] Int. Cl.$^5$ .............. C12N 15/16; C12N 15/70; C12N 1/21
[52] U.S. Cl. ............... 435/252.33; 435/69.4; 435/172.3; 435/320.1; 536/23.51
[58] Field of Search .............. 435/69.1, 69.4, 320.1, 435/172.3, 252.33; 536/23.51

[56] References Cited

U.S. PATENT DOCUMENTS

| | | | |
|---|---|---|---|
| 4,321,365 | 5/1982 | Wu et al. | 536/24.2 |
| 4,366,246 | 12/1982 | Riggs | 435/69.8 |
| 4,375,514 | 3/1983 | Siewert et al. | 435/172.3 |

FOREIGN PATENT DOCUMENTS

WO83/04028 11/1983 PCT Int'l Appl. .

OTHER PUBLICATIONS

Goodman et al., *Biochem Biophys Res Comm*, vol. 91(3) 1979, pp. 932-938, "Cell-free translation of messenger RNA coding for a precursor of human calcitonin".
Allison et al., *Biochem J.*, vol. 199, 1981, pp. 725-731, "The construction and partial characterization of plasmids containing complementary DNA sequence to human calcitonin polyprotein".
Amara et al., *PNC Natl Acad Sci*, vol. 77 (8), pp. 4444-4448, 1981, "Characterization of calcitonin mRNA".
Craig et al., *Nature*, vol. 295, Jun. 28, 1982, pp. 345-347, "Partial nucleotide sequence of human calcitonin precursor mRNA identities flanking cryptic peptides".

Primary Examiner—Richard A. Schwartz
Assistant Examiner—John LeGuyader
Attorney, Agent, or Firm—Elizabeth M. Barnhard; Marc S. Gross

[57] ABSTRACT

A precursor of a C-terminal amidated peptide represented by the general formula P-X-Gly-$Y_n$, wherein P is a peptide residue, X is an amino acid residue the C terminal of which (on the Gly side) can be converted in vivo to a —$CONH_2$ group, Gly is a glycine residue, Y is a basic amino acid residue, n is an interger of 2 to 4 and a further amino acid residue other than Y or a peptide residue may be attached to $Y_n$, is produced by a gene engineering technology. The precursor exhibits in vivo physiological activity like the C-terminal amidated peptide.

19 Claims, 12 Drawing Sheets

Fig. 2

Met-Cys-Gly-Asn-Leu-Ser-Thr-Cys-Val-Leu-Gly-Thr-Tyr-Thr-Gln-Asp-Phe-Asn-Lys-Phe-
    1               5              10              15

AATTC ATG TGT GGT AAC CTG AGC ACC TGT GTG CTG GGT ACC TAC ACC CAG GAT TTC AAC AAG TTC
G TAC ACA CCA TTG GAC TCG TGG ACA CAC GAC CCA TGG ATG TGG GTC CTA AAG TTG TTC  AAG
  2         4         6         7         8         10

His-Thr-Phe-Pro-Gln-Thr-Ala-Ile-Gly-Val-Gly-Ala-Pro-Gly-Lys-Lys-Arg-stop-stop
         25           30     32           17              36               19

CAC ACC TTC CCG CAG ACCGCT ATC GGT GTT GGT GCC CCG GGT AAG AAA GGC TAA TAG
GTG TGG AAG GGC GTC TGG CGA TAG CCA CAA CCA CGG GGC CCA TTC  TTT GCG ATT ATC CTAG
   12           13            14            16            18              20

Fig. 3

| A | | B | | C | |
|---|---|---|---|---|---|
| F 1) | AATTCATGTGT | F 8) | GAAATCCTGGGT | F 15) | ATCGGTGTTGGT |
| F 2) | GTTACCACACATG | F 9) | GATTTCAACAAG | F 16) | CGGGGCACCAAC |
| F 3) | GGTAACCTGAGC | F 10) | GTGGAACTTGTT | F 17) | GCCCCGGGTAAG |
| F 4) | ACAGGTGCTCAG | F 11) | TTCCACACCTTC | F 18) | CGTTTCTTACC |
| F 5) | ACCTGTGTGCTG | F 12) | CTGGGGAAGGT | F 19) | AAACGCTAATAG |
| F 6) | GTAGGTACCCAGCAC | F 13) | CCGCAGACCGCT | F 20) | GATCCTATTAG |
| F 7) | GGTACCTACACCCAG | F 14) | ACCGATAGCGGT | | |

200 →

150 →
140 →
118 →
100 →

82 →

66 →

PRECURSOR OF A C-TERMINAL AMIDATED CALCITONIN

This is a continuation of U.S. application Ser. No. 07/281,910, filed Dec. 7, 1988, now abandoned, which is a continuation of U.S. application Ser. No. 06/834,159, filed Feb. 27, 1986, now abandoned, which is a continuation of U.S. application Ser. No. 06/496,475 filed May 20, 1983, now abandoned.

This invention relates to a precursor of a peptide the C-terminal of which is amidated to a —$CONH_2$ group and a method of producing the same.

Among C-terminal amidated peptides, some are pharmacologically active. For instance, calcitonin is a peptide composed of a 32 amino acid residue with the C-terminal being in the amide form and is used for the treatment of hypercalcemia, osteoporosis and Behcet disease of the bone or for promoted osteogenesis. The amide form C-terminal structure is considered to be essential to activity development.

So far, pig, ox, sheep, human, rat, salmon and eel calcitonins have been isolated and the structure of each calcitonin has been elucidated. Among them, human, eel, pig and salmon calcitonins are now available on the market for therapeutic use. These are either extraction products from animal bodies or chemically synthesized products. However, the calcitonin content in animal bodies is low and the synthesis is difficult.

The present inventors intended to produce calcitonin on a large scale and at a low cost by using the gene manipulation technology. However, the present-day gene manipulation technology cannot afford C-terminal amidated peptides. Unexpectedly, it was found that precursors resulting from addition of glycine (Gly) to the amino acid which is to be amidated and further addition of two or more basic amino acids such as lysine (Lys) or arginine (Arg) also can produce pharmacological effects. The reason is presumably that the precursors are cleaved and modified in vivo under enzymatic actions to form C-terminal amidated peptides.

The present invention, which has been completed on the basis of this novel finding, provides, in one aspect thereof, a precursor of a C-terminal amidated peptide, which is represented by the general formula $$P-X-Gly-Y_n \quad (I)$$

wherein P is a peptide residue, X is an amino acid residue the C-terminal (on the Gly side) of which is capable of being converted in vivo to a —$CONH_2$ group, Gly is a glycine residue, Y is a basic amino acid residue, n is an integer of 2 to 4, and a further amino acid residue other than Y or a peptide residue may optionally be attached to $Y_n$.

Since, in vivo, X-Gly is presumably cleaved in the middle to yield a terminal-amidated peptide P-X-$NH_2$, adequate selection of the peptide residue P can give precursors corresponding to the desired terminal-amidated peptides, for instance calcitonin, oxytocin, vasopressin, LH-RH, melittin, eledoisin, secretin, kassinin, α-MSH, substance P, ranatensin, pancreatic polypeptide and VIP.

P-X may preferably be a peptide residue of the following formula (II):

Cys—$B^2$—Asn—Leu—Ser—Thr—Cys—$B^8$—Leu—$B^{10}$—$B^{11}$---$B^{27}$—Gly—$B^{29}$—$B^{30}$—$B^{31}$—Pro (II)

wherein, --- represents the 12th to 26th Bs, each B being independently a natural amino acid residue.

P-X may be a calcitonin residue and, in the above formula, $B^2$ may be Ser or Gly, $B^8$ may be Met or Val, $B^{10}$ may be Gly or Ser, $B^{11}$ may be Lys, Thr or Ala, $B^{12}$ may be Leu or Tyr, $B^{13}$ may be Thr, Ser or Trp, $B^{14}$ may be Gln, Arg or Lys, $B^{15}$ may be Glu, Asp or Asn, $B^{16}$ may be Leu or Phe, $B^{17}$ may be His or Asn, $B^{18}$ may be Lys or Asn, $B^{19}$ may be Leu, Phe or Tyr, $B^{20}$ may be Gln or His, $B^{21}$ may be Thr or Arg, $B^{22}$ may be Tyr or Phe, $B^{23}$ may be Pro or Ser, $B^{25}$ may be Thr or Met, $B^{26}$ may be Asn, Asp, Ala or Gly, $B^{27}$ may be Thr, Val, ILeu or Phe, $B^{29}$ may be Ser, Ala, Val or Pro, $B^{30}$ may be Gly or Glu and $B^{31}$ may be Val, Thr or Ala.

More specifically, P-X may be a calcitonin residue of the following formula (III):

Cys—Gly—Asn—Leu—Ser—Thr—Cys—W—Leu—  (III)
Gly—Thr—Tyr—Thr—Gln—Asp—Phe—Asn—
Lys—Phe—His—Thr—Phe—Pro—Gln—Thr—
Ala—Ile—Gly—Val—Gly—Ala—Pro wherein W is Val or Met.

The basic amino acid residue Y is a lysine or arginine residue. A preferred example of $Y_n$ is Lys-Lys-Arg-OH.

The above precursors can be produced by the method to be described hereinafter.

In another aspect, the present invention provides a gene which is a chemically synthesized double-stranded polynucleotide coding for the amino acid sequence of the above-mentioned calcitonin residue.

It is preferable that a codon for methionine is added to the head of the nucleotide sequence of the above gene and a translation-terminating codon to the tail thereof. Furthermore, it is preferable that a restriction enzyme-cleavable is further added to each end; for instance, an EcoRI cleavage site upstream (on the 5' side) and a BamHI cleavage site downstream (on the 3' side).

Furthermore, it is possible to introduce one or more restriction enzyme cleavage sites, for instance one or more RsaI, KpnI, SmaI and/or XmaI site or sites, into the nucleotide sequence.

Referring to the drawings, the figures are concerned with an embodiment of the present invention, which is to be described later by way of example. Thus, FIG. 1 illustrates, in the upper row, the amino acid sequence on which the synthetic gene designing is based and, in the lower row, the structure of mature calcitonin, with the portions in the lower row which are the same as those in the upper row being represented by line segments.

Figure 4:
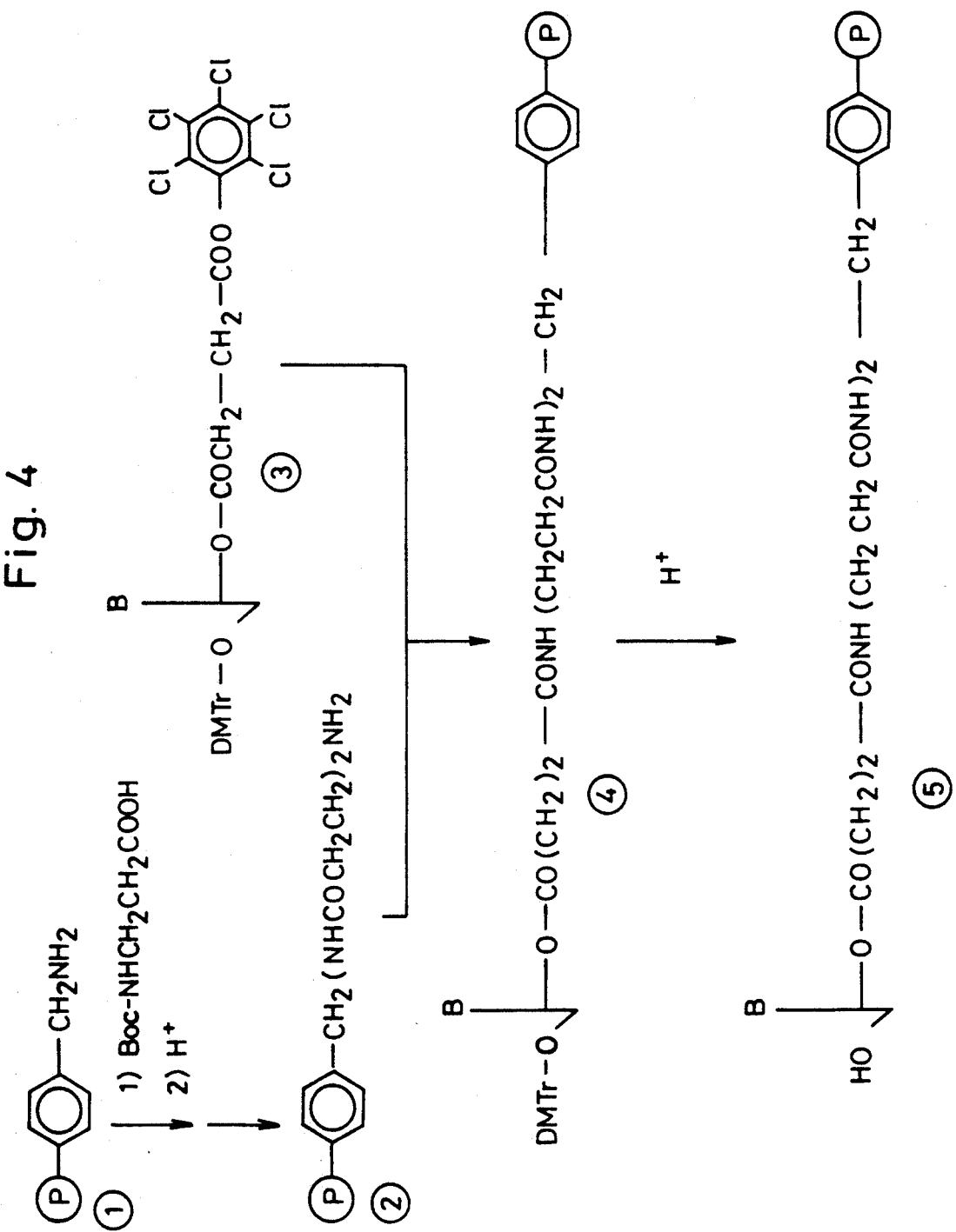
Figure 5:
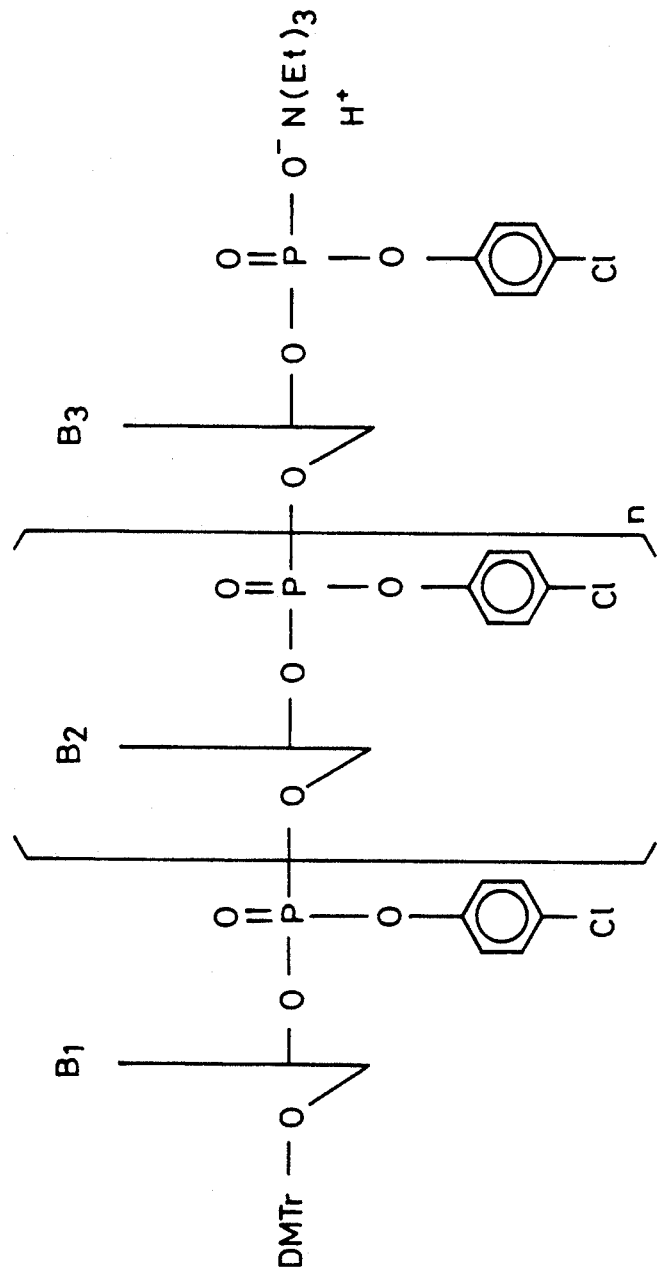
Figure 6:
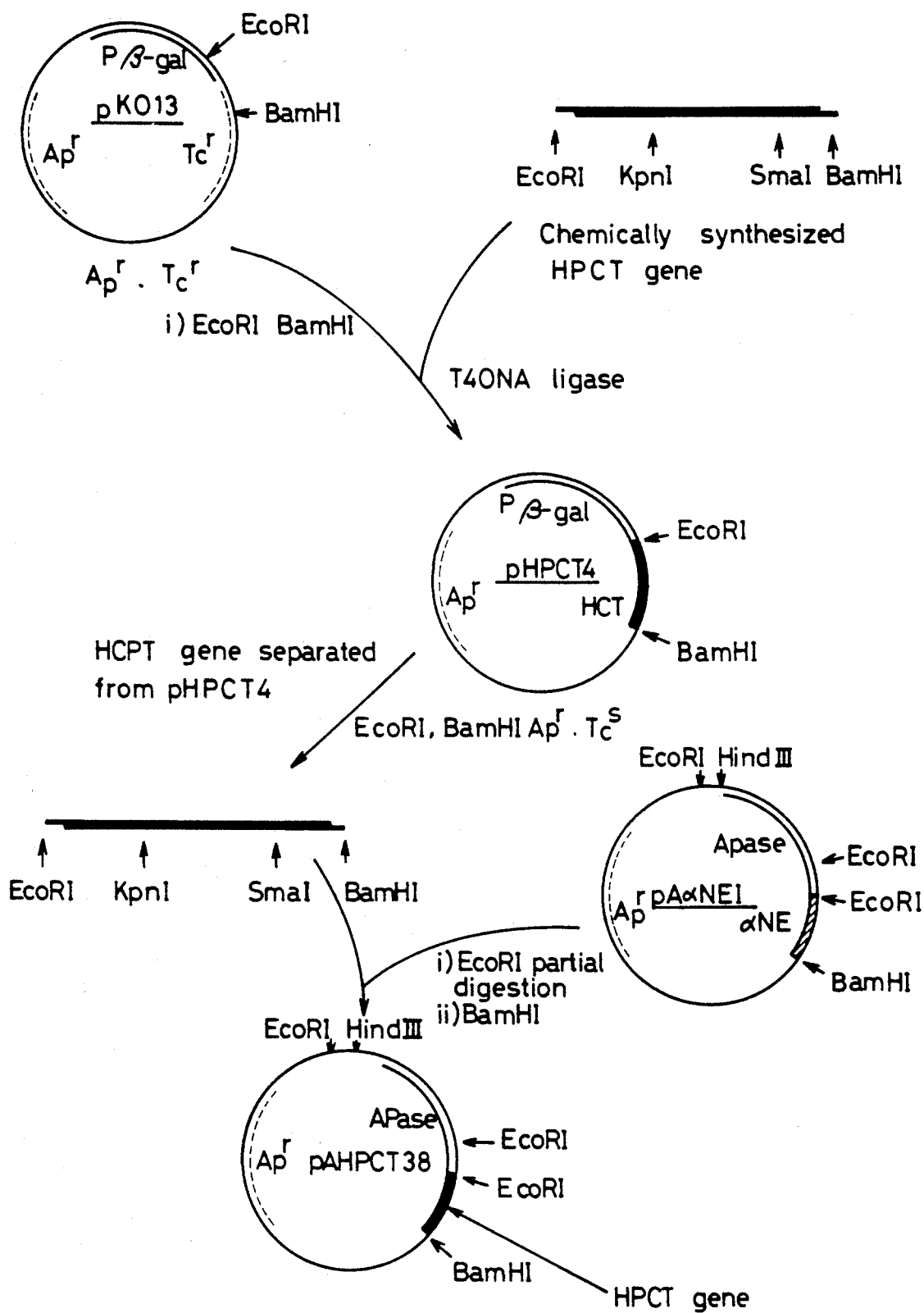
Figure 7:
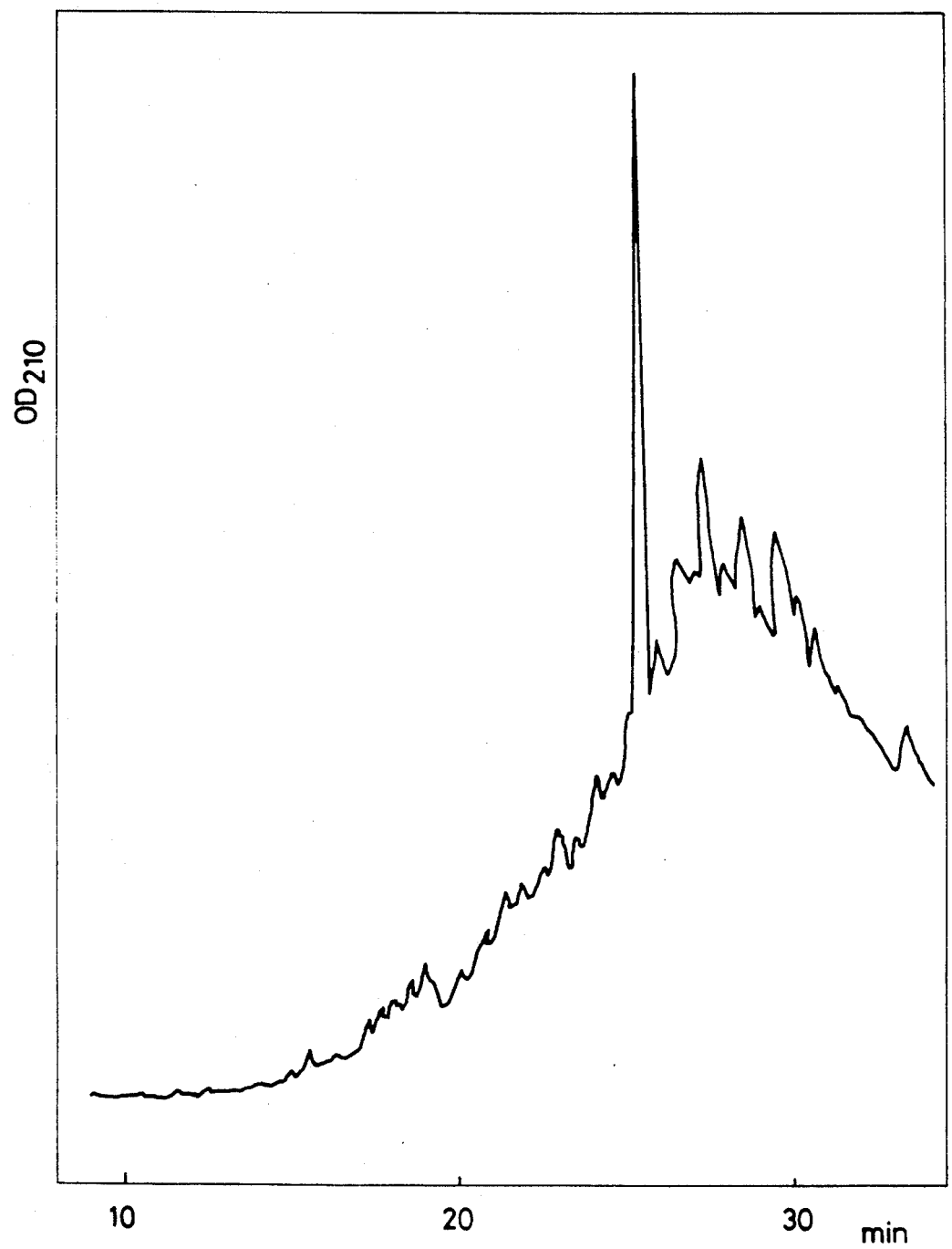
Figure 8:
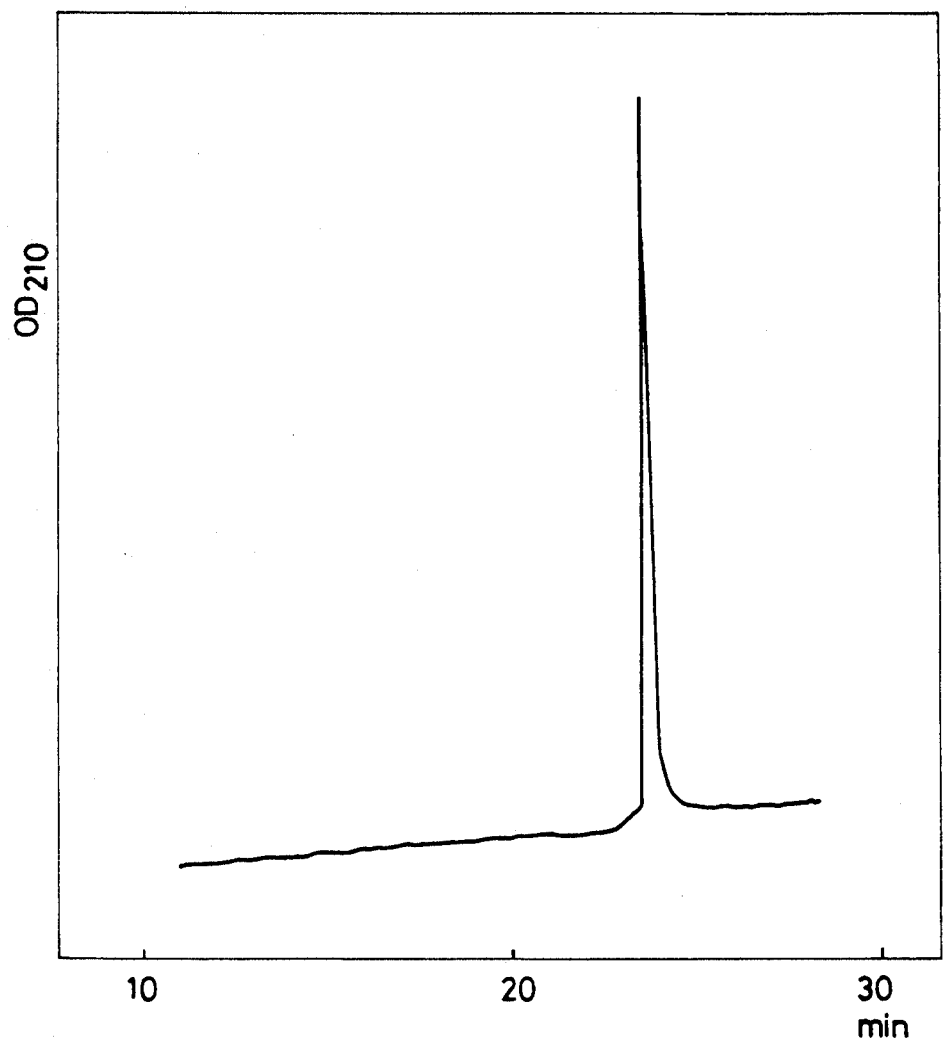

FIG. 2 shows the design of a gene, HPCT,

FIG. 3 shows the chemically synthesized fragments (F1 to F20) of the HPCT (1-36) gene, FIG. 4 shows the process for immobilizing a 3'-terminal mononucleotide unit on an aminomethylated polystyrene resin, FIG. 5 shows the structure of 3'-phosphodiester dimer (or trimer) blocks, FIG. 6 shows the process for constructing a recombinant plasmid containing the HPCT gene, FIG. 7 shows the HPLC elution pattern for HPCT produced by a bacterial strain transformed with the above-mentioned plasmid, and FIG. 8 shows the HPLC elution pattern for the fraction presenting a peak in FIG. 7.

Figure 9:
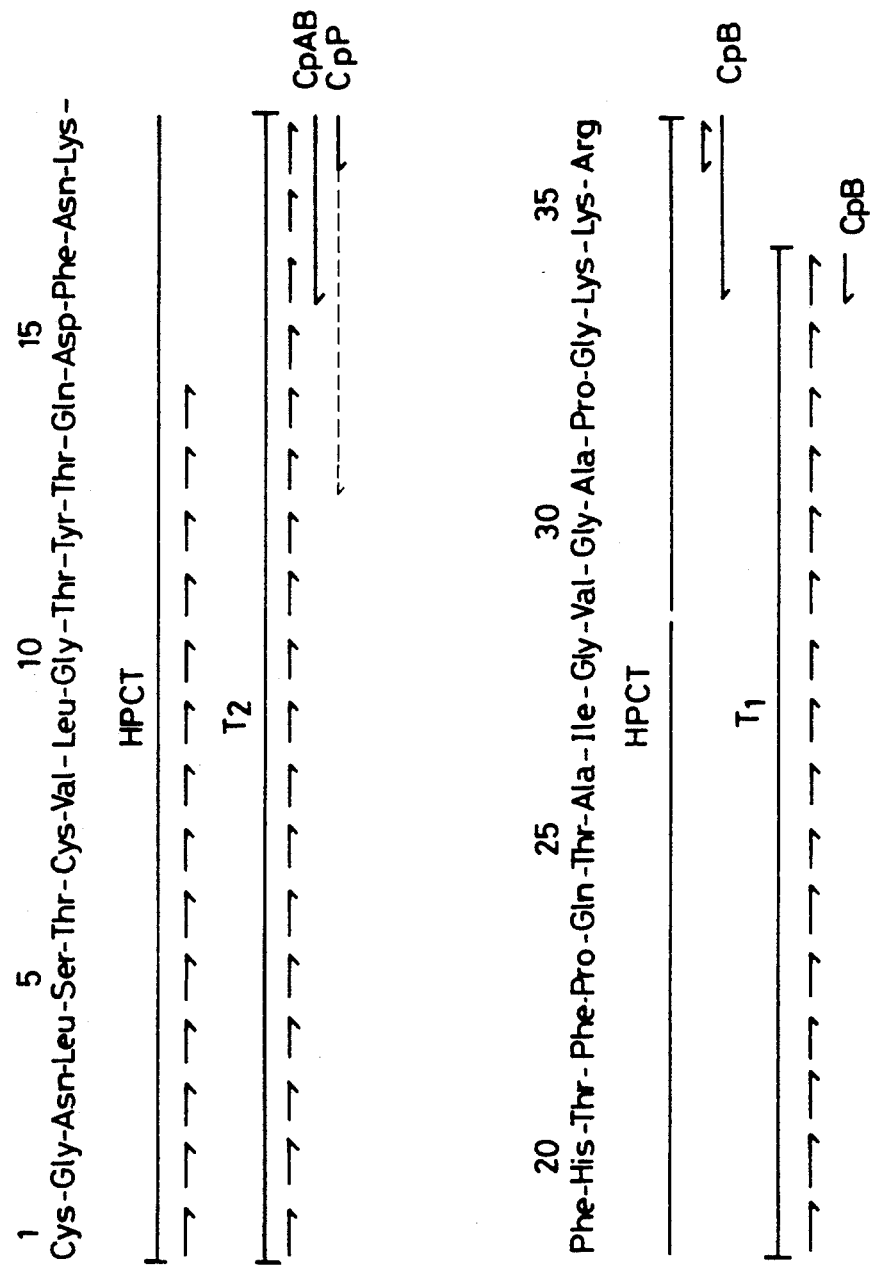

FIG. 9 shows the amino acid sequence of HPCT isolated by the above HPLC. In FIG. 9, Cp means carboxypeptidase, → denotes the amino acid sequence as determined by Edman's degradation method, — denotes the carboxy terminal portion amino acid sequence as determined by the carboxypeptidase method, --- denotes the carboxy terminal portion amino acid sequence as estimated by the carboxypeptidase method, and⟶ denotes the carboxy terminal as determined by the hydrazine decomposition method.

Figure 10:
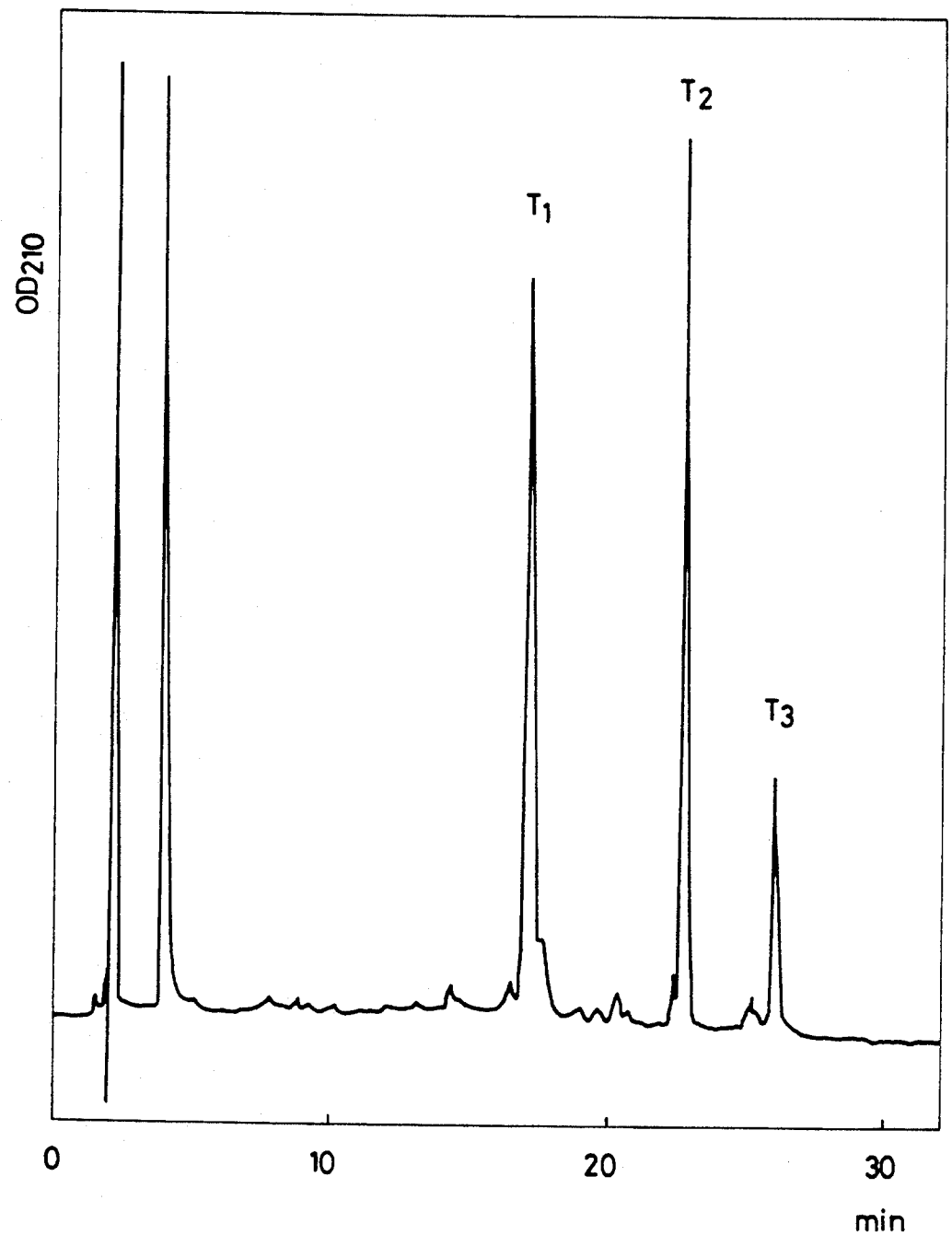
Figure 11:
Figure 12:
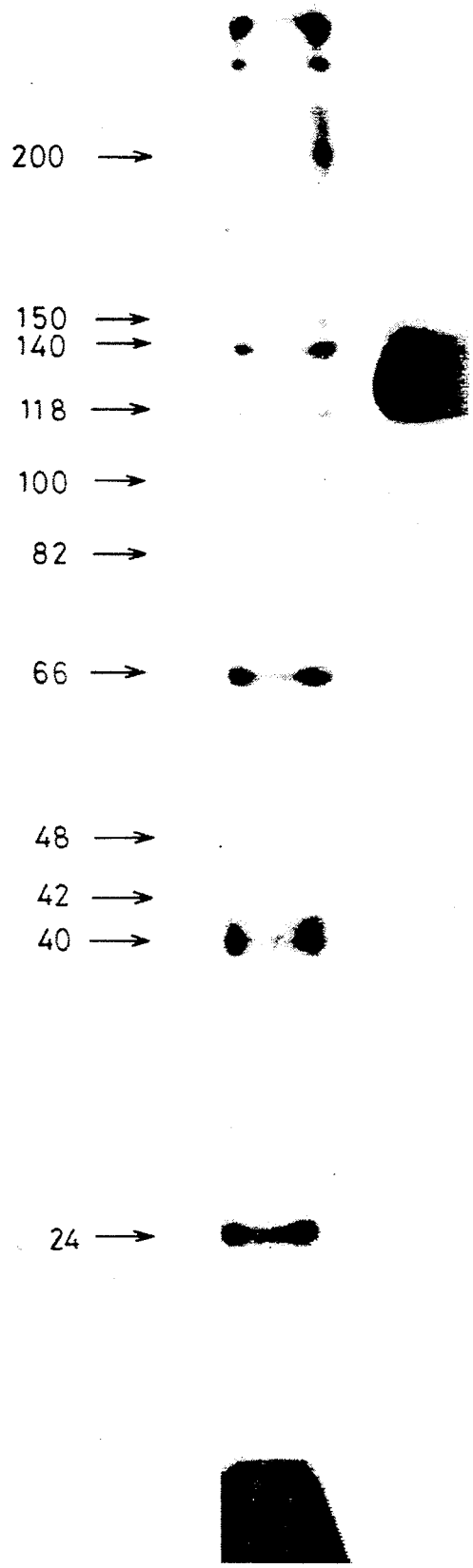

FIG. 10 shows the HPLC elution pattern for the tryptophan decomposition product from HPCT, and FIGS. 11 and 12 are the 8% polyacrylamide gel electrophoresis mappings for the gene synthesized from the oligonucleotide fragments F1 to F20.

A preferred example of the design of the double-stranded gene DNA is given in FIG. 2. The chemical synthesis of said gene is performed by first synthesizing the twenty DNA fragments F1 to F20 shown in FIG. 3 by the solid phase method (Miyoshi, K., Nucleic Acids Res., 8, 5507, 1980) and then preparing the double-stranded DNA from these fragments by the ligase reaction method.

In yet another aspect, the present invention provides a unicellular organism-derived or animal cell-derived plasmid or hybrid plasmid with a DNA containing the above gene and inserted therein.

An embodiment includes plasmids produced by connecting the above gene to a structural gene (e.g. APase or beta-galactosidase) in an operon containing a promoter-region derived from a unicellular organism, such as a microbe (e.g. bacterium, yeast, mold) or an animal cell such as monkey kidney cell, in a manner such that correct reading frame placement can be obtained. A preferred example is pAHPCT38 as illustrated in FIG. 6 cr pHPCT4 as shown in FIG. 6. pHPCT4 can be obtained by inserting the above chemically synthesized gene in between the EcoRI and BamHI cleavage sites cf pK013 (cf. Japanese Patent Application Sho 56-163303), while pAHPCT38 can be obtained by inserting the above chemically synthesized gene in between the EcoRI and BamHI cleavage sites of the plasmid pANE1 (cf. Japanese Patent Application Sho 56-170543) derived from an *Escherichia coli* alkaline . phosphatase (APase) gene-containing plasmid pBR322.

In a further aspect, the present invention relates to unicellular organisms or animal cells transformed with the above plasmid.

In an embodiment thereof, a transformant strain WA802/pHPCT could be obtained by transformation of an *Escherichia coli* strain K12 WA802 with the plasmid PHPCT4, and a transformant strain E15/pAHPCT could be obtained by transformation of an *Escherichia coli* strain K12.E15 with the plasmid pAHPCT38.

The strain E15 pAHPCT38 has been given a code name SBMC138 and deposited on May 6, 1982 with the Fermentation Research Institute, Agency of Industrial Science and Technology, 1-3, Higashi; 1 chome Yatabe-Mechi. Tsukuba-gun I baraki-hea 305, Japan, under Deposit No. FERM BP 283.

In a still further aspect, the present invention provides a method of producing a precursor of a C-terminal amidated peptide, which comprises cultivating host cells transformed with a plasmid with a therein-inserted gene having a nucleotide sequence coding for the amino acid sequence of a peptide of the above formula (I) with a code for Met added on the 5' end side thereof and having a subsequent nucleotide sequence coding for the termination of translation, and thereby causing formation of the above peptide as a protein component in the culture broth An example of the transformed host cells is the above-mentioned E15/pAHPCT. Taking this as an example, the method of cultivation is described. First, in a typical case, said transformant is cultured in a high phosphoric acid content medium and then transferred to a low phosphoric acid content medium, whereby APase is induced and the desired peptide precursor is formed as a protein component in the cells.

Preferred procedure and conditions of cultivation should preferably be selected depending on the plasmid species and host cell species.

After cultivation, the cells are separated from the culture, and treated with formic acid-cyanogen bromide. The desired fraction containing the desired peptide can be collected, for example, by density gradient fractional elution on an SP-Sephadex column using a pyridine-acetic acid buffer and purified by HPLC.

The thus-obtained precursor of C-terminal amidated peptide is as active as the C-terminal amidated peptide. For instance, the precursor HPCT shown in the upper part of FIG. 1 showed calcitonin activity, markedly reducing the calcium level in the rat blood. The abbreviation HPCT stands for a calcitonin precursor in which $Met^8$ of human calcitonin is replaced by Val.

EXAMPLE

Chemical Synthesis of HPCT Gene Fragment

The chemical synthesis of 20 oligodeoxyribonucleotides respectively designated $F_1$ through $F_{20}$ in FIG. 3, except for the improvements mentioned hereinafter, was carried out basically by the solid phase method reported by Ken-ichi Miyoshi et al [Nucl. Acids Res. 8, 5507 (1980)].

The outline of chemical synthesis of these oligodeoxyribonucleotides by the improved technology is as follows.

a) First, as shown in FIG. 4, the 3'-end mononucleoside unit was bound to an aminomethylated polystyrene resin. Thus, the aminomethylated polystyrene resin (1) shown in FIG. 4 is a resin cross-linked with 1% divinylbenzene, and the resin (2) was prepared by adding 2 units of beta-alanine to (1).

Then, three different compcunds (3) (B represents thymine, N-benzoylcytosine or N-isobutyrylguanine) were reacted with the above resin (2) to provide 3 different polystyrene resins (4) each carrying the 3'-end nucleoside The following is an example of synthesis of the same resin (4) relevant to thymine for B in FIG. 4.

Fifteen grams of aminomethylated polystyrene.HCl (divinylbenzene 1%, 100-200 mesh, $NH_2$: 0.63 m mol/g) was swollen well with 75 ml of $CH_2Cl_2$ and N-t-BOC-beta-alanine (1.01 g. 11.34 m moles) was added. The condensation reaction was conducted in the presence of DCC (2.34 g. 11.34 m moles) at room temperature for 3 hours. The resin was filtered through a glass filter and washed 4 times with 150 ml portions of $CH_2Cl_2$, 4 times with 150 ml portions of DMF and finally 4 times with 50 ml portions of pyridine. Then, the resin was treated with 75 ml of 25% acetic anhydride-pyridine for 30 minutes to acetylate the unreacted amino groups. Thereafter, the resin was treated with 90 ml of 20% $CF_3COOH$—$CH_2Cl_2$ at room temperature for 25 minutes to eliminate the t-BOC groups. The resin was washed with 150 ml of 5% triethylamine-$CH_2Cl_2$ and further washed 4 times with 50 ml portions of $CH_2Cl_2$. The above procedure was repeated for a second time to give the resin (2) of FIG. 4, i.e. the aminomethylated polystyrene resin having two β-alanine units. In 30 ml of DMF was suspended 5 g of the above resin [FIG. 4, (2)], followed by the addition of 5 m moles of compound (3) [FIG. 4, (3)] (where B means N-thynine) and 500 mg of triethylamine. The mixture was shaken at room temperature for 12 hours. After the reaction, the resin was filtered through a glass filter, washed with DMF and, then, with pyridine, and finally treated with 75 ml of 10% phenyl isocyanate-pyridine for 3 hours to protect the unreacted amino groups. The resin was subsequently washed with pyridine-methanol and dried under reduced pressure in the presence of $P_2O_5$, whereby the resin (4) of FIG. 4 (B means thymine) was obtained.

Using a portion of this resin (FIG. 4, (4), where B is thymine), the amount of 3'-end nucleoside secured to 1 gram of the resin was determined by the assay method of M. J. Gait et al [Nucl. Acids Res. 8, 1081 (1980)]. The result was 0.153 m mole. The resin (4) wherein B is N-benzoylcytosine or N-isobutylquanine was also prepared in the same manner as above. The amount of 3'-end nucleoside secured to 1 g of resin (4) was 0.150 m mole for B=N-benzoylcytosine and 0.147 m mole for B=N-isobutylguanine.

b) Using these three kinds of resin (4) and the 3'-phosphoric diester dimer block (FIG. 5, n=0) and 3'-phosphoric acid diester trimer block (FIG. 5, n=1), 20 oligodeoxyribonucleotides $F_1$ through $F_{20}$ having the specified predetermined base sequences. Thus, the resin (4) was treated with 2% benzenesulfonic acid ($CHCl_3$—MeOH=7:3, v,v) to remove the dimethoxytrytyl group (briefly, DMTr) and, then, 4 equivalents of 3'-phosphoric acid diester dimer (FIG. 5, n=0) or 3 equivalents of 3'-phosphoric acid diester trimer (FIG. 5, n=1) per equivalent of the 3'-nucleoside unit secured to resin (5) was sequentially condensed with the aid of 20 to 50 equivalents of mesitylenesulfonyltetrazolide (MsTe). The excess 3'-phosphoric acid diester block and condensing agent could be easily removed by filtering the reaction mixture through a glass filter.

Then, to protect the unreacted 5'-hydroxy group, the resin was treated with 10% acetic anhydride-pyridine at room temperature for 1 hour, whereby the unreacted 5'-hydroxy groups were acetylated. The resin was then treated with 2% benzenesulfonic acid ($CHCl_3$-MeOH=7:3, v/v) to remove the 5'-end DMTr group and, then, the next condensation reaction was conducted. The above procedure was repeated until the required length was obtained.

An exemplary sequence of synthesis is given below with reference to the $F_3$ fragment 200 mg of resin (4) [FIG. 4, (4), B=N-benzoylcytosine] was treated twice with 20 ml of 2% benzenesulfonic acid ($CHCl_3$—MeOH=7:3, v/v) (hereinafter abbreviated to 2% BSA) at room temperature for 1 minute each to give the resin (5) free from DMTr. To this resin (5) was added 90μ moles of the 3'-phosphoric acid trimer block GAG (FIG. 5, n=1, $B_1$=N-isobutyrylguanine, $B_2$=N-benzoyladenine, $B_3$=N-isobutyrylguanine) and the azotropic distillation with 3 ml of pyridine was repeated 3 times. Then, 2 ml of pyridine was added to the resin and the condensation reaction using 1 m mole of the condensing agent MsTe was carried out at room temperature for 2 hours. After the reaction, the excess 3'-phosphoric acid trimer and condensing agent could be easily removed by filtering the reaction mixture through a glass filter and washing the resin well with pyridine. Then, to protect the unreacted 5'-hydroxy groups, the resin was suspended in 20 ml of 10% acetic anhydride-pyridine and the suspension was shaken at room temperature for 1 hour. After this reaction, the resin was separated by filtration through a glass filter and washed well with pyridine and $CHCl_3$ in the order mentioned. Then, the resin was treated twice with 20 ml of 2% BSA ($CHCl_3$—MeOH=7:3, v/v) for 1 minute each, whereby the DMTr group was removed from the resin. The resin was washed well with $CHCl_3$ and pyridine in that order. The above procedure was repeated until the required length was obtained. Thus, to synthesize the oligodeoxyribonucleotide of $F_3$, the next 3'-phosphoric acid blocks CCT, AA and GGT were sequentially employed. By these sequential condensation reactions, a completely protected oligodeoxynucleotide-resin having the base sequence of $F_3$ was obtained The other frangments $F_1$, $F_2$ and $F_4$ to $F_{20}$ were also produced in the same manner except that different combinations of nucleotides were employed.

c) The severence of the completely protected oligodeoxyribonucleotide having such a definite base sequence from the resin and the complete deprotection thereof were carried out by treating the resin with concentrated aqueous ammonia-pyridine (2:1, v/v) at 55° C. for 10 hours and, then, with 80% acetic acid at room temperature for 10 minutes This deprotection procedure is described below with reference to $F_3$ fragment.

In a sealed tube, 50 mg of the $F_3$-resin was shaken with 1 ml of pyridine and 2 ml of concentrated aqueous ammonia at 55° C. for 10 hours, at the end of which time the resin was filtered off and the filtrate was cncentrated under reduced presure. To the residue was added toluene and the azeotropic distillation was repeated to remove the pyridine. The residue was treated with 2 ml of 80% acetic acid at room temperature for 10 minutes, whereby a completely deprotected oligodeoxyribonucleotide was obtained.

d) The isolation and purification of the final product was carried out by high performance liquid chromatography (briefly, HPLC). Thus, ALTEX Model 110 A Liquid Chromatograph, a linear gradient method using Solvent A (0.05M KH, pH 4.0) and Solvent B (0.05M $KH_2PO_4$-1.0M KCl, pH 4.0), and a Permaphase AAX (Du Pont) column (0.21×50 cm) were employed. The gradient was established by adding 3% of Solvent B to Solvent A at the intervals of 1 minute. Elution was carried out at 58° C. and a flow rate of 2 ml/min. The fractions containing the desired compound were pooled, desalted by dialysis and lyophilized. Each of the fragments thus obtained was further purified by HPLC on a linear gradient of Solvent A (0.01M EDA/2.5% acetonitrile, pH 7.0) and Solvent B (0.01M EDA/25% acetonitrile, pH 7.0) in a μ-Bondapak $C_{18}$ column (0.4×25 cm). The gradient was established by adding 3% of Solvent B to Solvent A at intervals of 1 minute. Elution was carried out at room temperature and a flow rate of 2 ml/min. The fractions containing the desired compounds were respectively pooled and lyophilized to obtain 20 DNA fragments $F_1$ through $F_{20}$.

e) The homogeniety of the 20 completely deprotected oligodeoxyribonucleotides $F_1$ through $F_{20}$ thus obtained was confirmed by labeling their 5'-ends with [gamma-$^{32}$P]ATP using $T_4$ polynucleotide kinase and carrying out polyacrylamide gel (20%) electrophoresis. The base sequence of each oligodeoxyribonucleotide was confirmed by the two-dimensional mapping method [Bambara, J. E. et al (1974) Nucl. Acids. Res. 1, 331]. Thus, the 5'-end was labeled with [gamma-$^{32}$P]ATP using $T_4$ polynucleotide kinase and, then, partial hydrolysis was carried with nuclease. This partial hydrolysate was subjected to cellulose acetate electrophoresis (pH 3.5) and DEAE-cellulose homochromatography.

Ligation of HPCT Gene Fragment

The 5'-ends of the chemically synthesized 18 oligonucleotide fragments ($F_2$ through $F_{19}$; FIG. 3) were phosphorylated and after $F_1$ and $F_{20}$ fragments were annealed, they were ligated by means of T4 DNA ligase to synthesize a gene corresponding to HPCT consisting of 122 base pairs. Details of the procedure are given below.

Excepting $F_1$ and $F_{20}$, 4.2 $\mu$g of each of the remaining 18 fragments was dissolved in 22 $\mu$l of distilled water and the solution was heated at 90° C. for 2 minutes and, then, immediately cooled to 0° C. To this aqueous solution was added 10 $\mu$Ci of $\gamma[^{32}P]$ ATP (5100 Ci/m mole). It was then adjusted to give a 50 mM Tris-HCl (pH 7.5)-10 mM $MgCl_2$-2 mM spermine-100 mM KCl-10 mM DTT oligonucleotide kinase buffer solution. Then, 3 units of polynucleotide kinase was added to make a total of 30 $\mu$l. By conducting the reaction at 37° C. for 15 minutes, the 5'-ends were labeled with $^{32}$P. Then, to phosphorylate all the 5'-ends, 4 n moles of ATP and 3 units of polynucleotide kinase were further added and the reaction was continued at 37° C. for 45 minutes. The reaction was terminated by heating the mixture at 90° C. for 5 minutes. 2.1 $\mu$g each of the above 18 phosphorylated fragments $F_2$ through $F_{19}$ and unphosphorylated fragments $F_1$ and $F_{20}$ were respectively mixed and dialyzed in a dialysis tube against distilled water at 4° C. for 16 hours to remove the unreacted ATP and kinase buffer components. This DNA dialyzate was concentrated to dryness and dissolved in 14.5 $\mu$l of ligase buffer (20 mM tris-HCl, pH 7.6, 10 mM $MgCl_2$). This solution was put in a 0.5 ml Eppendorf tube and heated at 95° C. for 2 minutes. Thereafter, the temperature was gradually lowered (to room temperature in 30 minutes) to anneal the 20 fragments. The reaction mixture was then held at 0° C. This DNA solution was made into a ligase, buffer containing 0.4 mM of ATP and 10 mM of DTT. Then, 30 units of T4 DNA ligase was added to make a total volume of 80 $\mu$l and the reaction was allowed to proceed at 11° C. for 16 hours. A portion of the reaction mixture was taken and subjected to electrophoresis with 18% polyacrylamide gel Using two kinds of gels, one containing 7M of urea and the other not containing urea, electrophoresis was carried out and the reaction product was analyzed by radioautography. It was found that a DNA corresponding to 122 base pairs had been produced at the rate of about 20 percent (FIGS. 11 and 12). Then, the entire amount of the above reaction mixture was fractionated by electrophoresis through 8% polyacrylamide gels. After the 122 base pairs of DNA were confirmed by radioautography, the corresponding portion of the gel was cut out and placed in dialysis tubes. Each tube was filled with 9 mM tris-borate (pH 8.3)-0.25 mM EDTA buffer and after closing both ends of the tube, electrophoresis was conducted in the buffer at a constant voltage cf 200-V for 3 hours to elute the DNA rom the gel. The DNA solution was taken out from the dialysis tube and lyophilized. The lyophilisate was dissolved in 100 $\mu$l of 0.3M sodium acetate (pH 7.0), and 2.5 volumes of ethanol was added. The mixture was allowed to stand at −80° C. for 30 minutes, at the end of which time it was centrifuged to recover the DNA sediments. The DNA thus obtained was dissolved in 30 $\mu$l of kinase buffer, 6 units of polynucleotide kinase and 0.8 nmol ATP were added, and the reaction was conducted at 37° C. for an hour. Thereafter, 3 $\mu$l of 3M sodium acetate was added, followed by 2.5 volumes of ethanol. There was thus obtained about 2 $\mu$g of the HPCT gene comprising 122 base pairs as the DNA precipitate.

Construction of Recombinant Plasmids

FIG. 6 illustrates the method of constructing recombinant plasmids containing the HPCT. The method is described hereinbelow in more detail.

(A) Construction of Plasmid pHPCT

The method of construction of the plasmid pK013 is as distinctly disclosed in the specification of Japanese Patent Application No. 163303/1981. The plasmid pK013 is a plasmid having most of the beta-galactosidase genes from the promoter region of the *Escherichia coli* lactose operon. The plasmid has one EcoRI and one BamHI cleavage site, and therefore genes obtained chemically or from natural sources and having EcoRI and BamHI cohesive ends can be easily inserted into the plasmid pK013. Furthermore, it is possible to cause the genes inserted downstream to the EcoRI cleavage site to express in terms of hybrid proteins with beta-galactosidase under the control of the lactose promoter. Following decomposition of the hybrid proteins with cyanogen bromide the desired peptides can be separated and purified.

Thus, 5 $\mu$g of pK013 was reacted at 37° C. for 60 minutes with 1 unit each of the restriction enzymes EcoRI and BamHI in 40 $\mu$l of 1×TA mixture (containing 33 mM Tris-acetate buffer, pH 7.6, 66 mM potassium acetate, 10 mM magnesium acetate and 0.5 mM dithiothreitol). The reaction mixture was heated at 65° C. for 30 minuites so as to inactivate the enzymes. Then, 0.7% agarose electrophoresis was carried out and large DNA fragments were recovered by electrophoresis. The resulting EcoRI/BamHI-cleaved fragment DNA of pK013 (1 $\mu$g) and 0.6 $\mu$g of the 5'-OH phosphorylated HPCT gene previously obtained were dissolved in 40 $\mu$l of T4 DNA ligation mixture (20 mM Tris-HCl buffer pH 7.6, 10 mM $MgCl_2$, 10 mM DTT, 0.4 mM ATP) and reacted with 2 units of T4 DNA ligase at 5° C. for 16 hours. To this reaction mixture was added 2.5 volumes of cold ethanol to give a DNA precipitate. This DNA was dissolved in 15 $\mu$l of distilled water and using 10 1 of the solution, it was introduced into *E. coli* WA802. The transformant was cultivated on a nutrient agar medium containing 40 $\mu$g/ml of ampicillin at 37° C. overnight and the colony formed was replicated on a nutrient agar medium containing 10 $\mu$g/ml of tetracycline to obtain tetracycline-sensitive colonies. The ampicillin-resistant, tetracycline-sensitive transformants thus obtained were designated as WA802/pHPCT1 through WA802/pHPCT5. The DNA base sequence of the small EcoRI/BamHI cleaved DNA fragment obtained from WA802/pHPCT4 was analyzed by the procedure described below to find that the pHPCT4 plasmid had the DNA base sequence of the desired HPCT gene.

In this WA802/pHPCT4 strain, HPCT is expressed as a β-galactosidase-HPCT hybrid protein under the control of the lactose promoter and the HPCT can be separated as a complete peptide desired from this hybrid protein by methionine decomposition with cyanogen bromide. However, since the β-galactosidase protein contains 23 methionine residues, a number of unnecessary impurity peptides are produced in the cyanogen bromide decomposition, thus interfering with the separation and purification of the desired peptide. Therefore, we developed as a vector free from the above disadvantage a plasmid derived from the *E. coli* alkaline phosphatase gene and established its usefulness (Japanese Patent Application No. 70543/1981). Therefore, in the thought that for the separation and purification of the HPCT peptide from *Escherichia coli*, it is more desirable to construct a plasmid by recombination of the alkaline phosphatase gene-based plasmid with the HPCT gene, we performed the construction of such a plasmid as follows.

The HPCT base sequence in the plasmid carried by the above transformant strains was analyzed in the following manner.

HPCT Base Sequence

Each (150 μg) of the plasmid DNAs, pHPCT1, pHPCT2, pHPCT3 and pHPCT4, was digested with 200 units of the restriction enzyme EcoRI and 200 units of the restriction enzyme SalI, and a DNA fragment comprising about 400 base pairs inclusive of the PHCT gene was separated and purified. Then, the 5'-end was dephosphorylated with bacterial alkaline phosphatase, and the 5'-end was labeled with $^{32}P$ using γ-[$^{32}P$]ATP and polynucleokinase. Thereafter, digestion was conducted with 100 units of the restriction enzyme BamHI, and a DNA fragment comprising 122 base pairs was separated and purified and subjected to base sequencing by the Maxam-Gilbert method (Proc. Natl. Acad. Sci., U.S.A., 74, 560–564, 1977). As a result, it was confirmed that all the plasmids except for pHPCT1 had the base sequence as initially designed. In pHPCT1, the third member (C) of the codon (AAC) corresponding to the 17th amino acid of HPCT, namely asparagine, had been substituted by T. Nevertheless, the codon AAT also corresponds to asparagine.

(B) Construction of Plasmid pAHPCT38

The method of constructing plasmid pAαNE1 is detailed in the specification of Japanese Patent Application No. 170543/1981. pAαNE1 is a plasmid prepared by incorporating an α-neoendorphin gene downstream of the EcoRI cleavage site of an *E. coli* alkaline phosphatase structural gene, and is a vector which expresses an alkaline phosphatase alpha-neoendorphin hybrid protein under the expression and modulation control of alkaline phosphatase. The procedure for construction of plasmid pAHPCT38 containing an HPCT gene in place of the alpha- o neoendorphin gene is described in detail below.

In 100 μl of 1×TA mixture, 10 μl of plasmid pAα-NE1 was partially cleaved using 10 units of the restriction enzyme EcoRI at 37° C. for 30 minutes. Then, 0.7% agarose gel electrophoresis was carried out and the DNA fragment cleaved by EcoRI at one site only was recovered by electrophoresis. The DNA fragment thus recovered was completely cleaved in 30 μl of 1×TA using 5 units of the restriction enzyme BamHI at 37° C. for 60 minutes, after which 2.5 volumes of cold ethanol was added thereto so as to precipitate the DNA. This DNA precipitate was dissolved in 30 μl of distilled water. In 30 μl of T4 DNA ligation medium was dissolved 0.5 μg of this EcoRI/BamHI-cleaved DNA fragment together with 0.5 μg of an HPCT gene DNA prepared from pHPCT4 using EcoRI and BamHI, and ligation was conducted using 2 units of T4 DNA ligase at 5° C. for 16 hours. To the reaction mixture was added 2.5 volumes of cold ethanol to give a DNA precipitate. This DNA precipitate was dissolved by addition of 10 μl of distilled water and introduced into *Escherichia coli* E15 [Hayashi et al: J. Biol. Chem. 239, 3091 (1964)]. Each transformant strain was incubated on a nutrient agar medium containing 40 μg/ml of ampicillin at 37° C. overnight. The 72 ampicillin-resistant strains obtained in the above manner were examined for the existence of SmaI-cleaved sites in plasmids. It was found that 3 strains are found to carry plasmids having SmaI-cleaved sites within the HPCT gene. One of these strains was represented as E15/pAHPCT38 and used in the next separation and purification f HPCT peptide.

The above *Escherichia coli* E15/pAHPCT38 has been deposited with the Fermentation Research Institute, the Agency of Industrial Science and Technology under the deposit number of FERM BP 283.

Purification of a Human Calcitonin Precursor from *E. coli* E15/pAHPCT38

In *E. coli* E15/pAHPCT38, the HPCT gene was inserted into the alkaline phosphatase structural gene. Therefore, HPCT was expected to be expressed as a protein hybridized with alkaline phosphatase. However, as shown in the initial HPCT gene design, by inserting methionine at the N-terminal of HPCT and by cleaving this alkaline phosphatase-HPCT hybrid protein with cyanogen bromide, HPCT can be easily obtained. Therefore, the separation and purification of HPCT from *E. coli* K12E15/pAHPCT38 was performed by the procedure described in detail hereinafter. As to the cultivation of *E. coli* K12E15/pAHPCT38 and the induction of the alkaline phosphatase-HPCT hybrid protein, these were conducted in accordance with the methods described in the specification of Japanese Patent Application Nc. 170543/1981.

The *E. coli* E15/pAHPCT38 strain was incubated in 100 ml of TG+20 (phosphate-r.ch medium) containing 40 μg/μl of ampicillin at 37° C. for 16 hours and the culture was used to inoculate 10 l of TG+1 (phosphate-lean medium) and further incubated at 37° C. for 24 hours. The cells were collected by centrifugation to recover 2.36 g of moist cells. The ceils were suspended in 20 ml of a 70% formic acid solution containing 500 mg of cyanogen bromide and allowed to stand in the dark at room temperature for 24 hours.

Purification of HPCT from *E. coli* E15/pAHPCT1

The cyanogen bromide-treated cell suspension was lyophilized and after addition of 60 ml of distilled water, it was ultrasonicated at room temperature for about an hour. The resulting suspension was centrifuged (10,000 r.p.m., 15 min.) and with the supernatant kept undiscarded, the sediment was diluted with 30 ml of distilled water, ultrasonicated again and centrifuged. The supernatant was combined with the previous supernatant to give 90 ml. This solution was made up to 100 ml with 10 ml of distilled water and passed through an SP-Sephadex C-25 column (1.4×20 cm). The column was previously equilibrated with 0.025M acetic acid and after application of the sample, it was washed with 230 ml of the same acetic acid solution and, then, with 200 ml of 1.5% pyridine-acetate buffer (briefly, PA buffer) (pH 4.47) and 160 ml of 2.5% PA buffer (pH 4.65). Thereafter, elution with 60 ml of 2.5% PA buffer (pH 4.65) and 60 ml of 3.75% PA buffer (pH 4.76) was carried out by the linear gradient method, followed by further elution with 60 ml of the latter buffer and still further elution on a linear gradient using 160 ml of 3.75% PA buffer (pH 4.76) and 160 ml of 5.0% PA buffer (pH 4.87), the eluate being collected in 6 ml fractions. At the interval of several tubes, a 100 μl portion of each fraction was subjected to HPLC analysis. (The conditions of HPLC are mentioned hereinafter.) The fractions corresponding to the main peaks on HPLC were respectively evaporated to dryness, dissolved in 150 ml of 6N hydrochloric acid containing 0.1% phenol, and hydrolyzed at 110° C. for 24 hours. The hydrolysate was evaporated to dryness and submitted to amino acid analysis (Hitachi #835-50 Amino Acid Analyzer) to monitor the state of elution from the column. As a result, the presence of HPCT was confirmed in the entire 2.5%–3.75% gradient eluate (total, 120 ml), the entire 3.75% PA buffer eluate (60 ml), and the first 10 fractions (60 ml) in the 3.75%–5.0% gradient eluate.

These HPCT-containing fractions were pooled and lyophilized, and the purification thereof by HPLC was carried out.

The above dried product was dissolved in 8.0 ml of 0.1N acetic acid and 100 to 300 μl portions thereof were purified by means of μ-Bondapack $C_{18}$ (Waters) columns (0.39×30 cm). Elution was carried out by the linear gradient method using 0.1% trifluoroacetic acid containing 10% of acetonitrile and 0.1% trifluoroacetic acid containing 50% of acetonitrile and the state of elution was monitored at the UV wavelength of 210 nm. As shown by the typical chromatogram in FIG. 7, the peak corresponding to HPCT can be clearly detected. The fractions containing such peaks were pooled and HPLC under the same conditions was performed again (FIG. 8) to obtain 2.15mg (0.56 μmole) of pure HPTC.

Structural Identification of HPCT

The amino acid composition of HPCT was determined on the basis of the amino acid analysis of the hydrolysate of HPCT prepared by hydrolyzing HPCT with 6N hydrochloric acid containing 0.1% of phenol in a sealed tube and the result of an amino acid analysis conducted after HPCT was oxidized with performic acid and hydrolyzed with 6N HCl at 110° C. for 24 hours in the conventional manner (1) (Table 1). The amino acid sequence of the performic acid oxidation product of HPCT was analyzed by Edman's degradation method (2), whereby the sequence to the 15th residue from the N-terminal could be determined (FIG. 9). Then, in order to determine the amino acid sequence of total HPCT, HPCT was degraded with trypsin in the hope of obtaining fragment peptides.

In 30 μl of 0.1N PA buffer (pH 7.80) was suspended 160 μg of HPCT and after 30 minutes of ultrasonic treatment, 10 μl of TPCK-treated trypsin solution (3) (1 mg/ml) was added. The mixture was allowed to stand at 37° C. for 2 hours. The reaction mixture was then lyophilized, dissolved in 400 μl of 0.1N acetic acid, and subjected to HPLC. The conditions of HPLC used here were exactly identical with those used in the purification of HPCT and the chromatogram monitored at the UV wavelength of 210 nm was as reproduced in FIG. 10. Thus, the amino acid compositions of the peaks $T_1$, $T_2$ and $T_3$ suggested that $T_1$ was a peptide from the 19th amino acid unit of HPCT through the 34th amino acid unit, $T_2$ was a peptide from the N-terminal through the 18th amino acid unit, and $T_3$ was a peptide from the N-terminal through the 34th amino acid unit (Table 1).

The literature references mentioned in the foregoing are as follows.
(1) C. H. W. Hirs, "Methods in Enzymology", Academic Press, New York, Vol. 11, P. 197 (1967)
(2) J. P. Van Eerd et al., Biochemistry, 15, 1171 (1976)
(3) S.-S. Wang et al., J. Biol. Chem., 240, 1619 (1965)

Then, the amino acid sequence analysis was carried out using $T_1$ and the performic acid oxidation product $T_2$ (FIG. 9). Moreover, the amino acid sequence analysis of the C-terminal ends of HPCT, $T_1$, and $T_2$ was carried out by the carboxypeptidase method [T. Isobe et al.: J. Mol. Biol., 102, 349 (1976)], and the C-terminal analysis thereof was carried out by the hydrazine method [A. Tsugita et al.: Proc. Nat. Acad. Sci., U.S.A., 46, 1462 (1960)] (FIG. 9). Based on results of the above analyses, the amino acid sequence of HPCT was identified as shown in FIG. 9.

Purification of HPCT-Cp(1-33), the Carboxypeptidase Degradation Product

In 300 μl of 0.1N PA buffer (pH 7.80) was suspended 500 μg of HPCT and after 1 hour of ultrasonication, 7.5 μl of carboxypeptidase B solution (0.67 mg/ml) was added. The mixture was allowed to stand at 37° C. for 6 hours. The liberated amino acids (2 moles of lysine and 1 mole of arginine) were detected by amino acid analysis. The reaction mixture was then lyophilized, dissolved in 500 μl of 0.1 acetic acid and purified by HPLC. The conditions of HPLC were identical with those used in the purification of HPTC and the chromatogram was monitored at the UV wavelength of 210 nm. Amino acid analysis of the peptide thus purified showed that it is a peptide from the N-terminal through the 33rd amino acid, i.e. HPCT.Cp(1-33) (Table 1). The yield calculated from the amino acid analysis data was 302 μg or 68%.

TABLE 1

The Amino Acid Compositions of HPCT, $T_1$, $T_2$ and HPCT-Cp (1-33)

|  | HPCT | $T_1$ | $T_2$ | HPCT-Cp (1-33) |
|---|---|---|---|---|
| $CySO_3H$ | 1.6 |  | 1.8 | 1.9 |
| Asp | 3.1 |  | 3.0 | 3.0 |
| Thr | 4.7 | 1.8 | 2.8 | 4.7 |
| Ser | 1.1 |  | 1.1 | 1.0 |
| Glu | 2.0 | 1.0 | 1.1 | 2.1 |
| Pro | 2.0 | 1.9 |  | 1.9 |
| Gly | 4.8 | 2.8 | 2.0 | 5 |
| Ala | 2.2 | 1.9 |  | 2.1 |
| Val | 1.9 | 1.0 | 1.0 | 2.0 |
| Ile | 1.1 | 1.0 |  | 1.1 |
| Leu | 2 |  | 1.9 | 2.0 |
| Tyr | 1.0 |  | 1.0 | 1.0 |
| Phe | 2.7 | 1.9 | 1.1 | 3.0 |
| Lys | 2.9 | 1 | 1 | 1.1 |
| His | 0.9 | 0.9 |  | 1.0 |
| Arg | 1.0 |  |  |  |
|  | 36 | 16 | 18 | 33 |

In the table, the underscore figures were used to calculate the figures for other amino acids.

Biological Activity of HPCT

The biological activities of HPCT and HPCT Cp(1-3S) purified by the above-mentioned procedure were assayed using the serum calcium lowering effect in rats as an indicator.

Procedure

Male Wistar strain rats weighing 300 to 350 grams were fasted overnight and used. Each animal was secured in supine position and under ether anesthesia, a polyethylene tube (Intramedic ® PE-50, Clay Adams) filled with heparin sodium injection J. P. (Japan-Upjohn) was inserted into the femoral artery of the right hind leg. The rat was fixed in a Boleman cage, and 30 minutes after awakening of the animal, 0.5 ml of the blood was withdrawn through the above polyethylene tube inserted into the femoral artery into a polyethylene centrifugal tube containing 50 units of heparin sodium. Immediately thereafter 0.2 ml of the under-mentioned physiological saline, HPCT. HPCT.Cp(1-33) or swine calcitonin solution was administered subcutaneously at the back of the animal. Then, 1, 2, 4 and 6 hours after the administration, 0.5 ml each of the blood was taken through the above-mentioned polyethylene tube. The blood thus taken was promptly centrifuged on an Eppendorf microcentrifuge (Eppendorf 5414) at 13,000 r.p.m. for 1 minute and the supernatant was used as serum fraction.

The blood calcium level was measured by the o-cresolphthalein complexon method using a commercial calcium assay kit RM117-K (Ca SET) (Yatron). Fifty μl of the serum was taken in a test tube and stirred with 0.5 ml of the color reagent containing o-cresolphthalein complexon and 8-hydroxyquinoline (RM117-2). Then, 5.0 ml of monoethanolamine borate buffer (RM117-1) was added and stirred. Within 90 minutes thereafter, the absorbance was measured with a self-recording spectrophotometer (Hitachi 320) at the wavelength of 575 mu. The concentration of calcium was calculated from this absorbance value.

The methods used in the preparation of the physiological saline solution, HPCT solution, HPCT. Cp(1-3S) solution and swine calcitonin solution employed are as follows.

a) Physiological saline solution: Bovine serum albumin (Sigma ®) was dissolved in physiological saline J. P. (Ohtsuka Pharmaceutical Co.) at room temperature to the albumin concentration of 0.1%.

b) HPCT solution: HPCT was diluted with the above-mentioned physiological saline solution containing 0.1% of albumin to the HPCT concentration of 4.5 μg/0.2 ml.

c) HPCT Cp(1-33) solution: HPCT Cp(1-33) was diluted with the above-mentioned physiological saline solution containing 0.1% of albumine to the HPCT Cp(1-33) concentration of 20 μg/0.2 ml.

d) Swine calcitonin solution: Calcital ® for Injection (Yamanouchi Pharmaceutical Co.) containing 160 I.U. of calcitonin per vial was dissolved in 40 ml of a vehicle containing 16% of purified gelatin and 0.5% phenol J. P. and the solution was diluted with the above-mentioned physiological saline solution containing 0.1% of albumin. This dilution contained 0.2 or 1 I.U. of swine calcitonin per 0.2 ml.

Results

The results are shown in Table 2. The serum calcium level of the rat treated subcutaneously with 4.5 μg of HPCT dropped with statistical significance in 1 and 2 hours after the administration. The time course of serum calcium concentration after HPCT treatment was very similar to the time course of serum calcium observed in the rat subcutaneously given 0.2 I.U. of swine calcitonin. It was therefore considered that under the above experimental conditions 4.5 μg of HPCT is equivalent in activity to 0.2 I.U. of swine calcitonin.

The serum calcium level of the rat treated subcutaneously with 20 μg of HPCT.Cp(1-33) dropped with statistical significance in 1 hour after the administration, however, no dropping of the serum calcium level was observed in the course of 2 hours after the administration.

With respect to calcitonins, it is known that compared with naturally-occurring peptides having amidated C-terminals, peptides with free C-terminals (desamidopeptides) are generally very low in biological activity. However, HPCT (a precursor of $Val^8$ human calcitonin) and HPCT Cp(1-33) suggest their stronger physiological activity as compared with swine calcitonin as shown in Table 2, though they can not be compared in an equal amount because the weight of the swine calcitonin in the Table is not clear.

Moreover, although much research has been done into the substitution of amino acids in the amino acid sequence of calcitonin and the partial elimination of peptides or amino acids from the sequence, it has never been known that the addition of a peptide as in this invention has ever given rise to an active substance.

TABLE 2

Influence of HPCT on Rat Serum Calcium

| | Change in serum Ca level (mg/dl) | | | |
|---|---|---|---|---|
| | 1 hour | 2 hours | 3 hours | 4 hours |
| Physiological saline | −0.01 ± 0.03 | −0.12 ± 0.08 | −0.31 ± 0.08 | −0.45 ± 0.07 |
| HPCT (4.5 μg/rat) | −0.85 ± 0.09[b] | −0.64 ± 0.08[b] | −0.47 ± 0.05 | −0.63 ± 0.11 |
| HPCT.Cp (1-33) (20 μg/rat) | −0.82 ± 0.20[a] | −0.28 ± 0.17 | −0.21 ± 0.08 | −0.25 ± 0.11 |
| Swine calcitonin 0.2 I.U./rat | −0.70 ± 0.19[a] | −0.71 ± 0.07[b] | −0.49 ± 0.06 | −0.60 ± 0.12 |
| Swine calcitonin (1.0 I.U./rat) | −0.67 ± 0.08[b] | −0.93 ± 0.06[b] | −1.25 ± 0.06[b] | −0.88 ± 0.14 |

The figures are the mean values for 4 rats per group = standard deviations.
[a]Significant difference at ≦5% level from physiological saline control
[b]Significant difference at ≦1% level from physiological saline control

What is claimed is:

1. A chemically synthesized gene encoding a pharmacologically active calcitonin precursor comprising a chemically synthesized polynucleotide which codes on expression for the amino acid sequence:

Cys—Gly—Asn—Leu—Ser—Thr—Cys—Val—Leu—
    Gly—Thr—Tyr—Thr—Gln—Asp—Phe—Asn—Lys—
    Phe—His—Thr—Phe—Pro—Gln—Thr—Ala—Ile—
    Gly—Val—Gly—Ala—Pro—Gly—Lys—Lys—Arg.

2. The gene according to claim 1, wherein a codon for methionine is added to the 5'end of the nucleotide sequence of at least one translation-terminating codon is added to the 3' end thereof.

3. The gene according to claim 1 or claim 2, wherein one end of the gene is an EcoRI cohesive end, and the other end is a BamHI cohesive end.

4. The gene according to claim 1, wherein at least one of RsaI, KpnI, SmaI and XmaI cleavage sites is present in the nucleotide sequence.

5. A gene comprising a chemically synthesized polynucleotide which comprises the sequence:

```
5'
TGT GGT AAC CTG AGC ACC TGT GTG CTG GGT ACC TAC ACC CAG
ACA CCA TTG GAC TCG TGG ACA CAC GAC CCA TGG ATG TGG GTC
GAT TTC AAC AAG TTC CAC ACC TTC CCG CAG ACC GCT ATC GGT
CTA AAG TTG TTC AAG GTG TGG AAG GGC GTC TGG CGA TAG CCA
                                                       3'
GTT GGT GCC CCG GGT AAG AAA CGC
CAA CCA CGG GGC CCA TTC TTT GCG.
``` which codes on expression for a pharmacologically active calcitonin precursor.

6. The gene according to claim 5, further comprising a codon for methionine at the 5' end of the nucleotide sequence of the gene and at least one translation-terminating codon at the 3' end thereof.

7. The gene according to claim 5 or claim 6, wherein one end of the gene is an EcoRI cohesive end, and the other end is a BamHI cohesive end.

8. The gene according to claim 5 or claim 6, wherein at least one of RsaI, KpnI, SmaI, and XmaI cleavage sites is present in the nucleotide sequence.

9. A plasmid including an insert comprising, in sequence, a promoter region and an *Escherichia coli* structural gene, and a gene encoding a pharmacologically active calcitonin precursor which encodes on expression for the following amino acid sequence:

Cys—Gly—Asn—Leu—Ser—Thr—Cys—Val—Leu—Gly—
Thr—Tyr—Thr—Gln—Asp—Phe—Asn—Lys—Phe—His—
Thr—Phe—Pro—Gln—Thr—Ala—Ile—Gly—Val—Gly—
Ala—Pro—Gly—Lys—Lys—Arg.

wherein the insert has EcoRI and BamHI cohesive ends.

10. The plasmid according to claim 9, wherein the structural gene codes on expression for an *Escherichia coli* alkaline phosphatase or beta-galactosidase and is ligated to the gene encoding the precursor so that correct reading frame is obtained.

11. The plasmid according to claim 9, which is pAHPCT38.

12. A plasmid which comprises, in sequence, a promoter region, a structural gene, a methionine codon and a polynucleotide of the sequence:

```
5'
TGT GGT AAC CTG AGC ACC TGT GTG CTG GGT ACC TAC ACC CAG
ACA CCA TTG GAC TCG TGG ACA CAC GAC CCA TGG ATG TGG GTC
GAT TTC AAC AAG TTC CAC ACC TTC CCG CAG ACC GCT ATC GGT
CTA AAG TTG TTC AAG GTG TGG AAG GGC GTC TGG CGA TAG CCA
                                                       3'
GTT GGT GCC CCG GGT AAG AAA CGC
CAA CCA CGG GGC CCA TTC TTT GCG.
``` wherein the promoter region, structural gene and polynucleotide are in the same reading frame.

13. The plasmid according to claim 12, wherein the structural gene is alkaline phosphatase or beta-galactosidase.

14. The plasmid according to claim 12 or claim 13, which is pAHPCT38.

15. An *Escherichia coli* transformant with the plasmid of claim 9.

16. The *Escherichia coli* according to claim 15, wherein the plasmid is pAHPCT38.

17. An *Escherichia coli* transformed strain of claim 15, namely the strain E15/pAHPCT38 (Fermentation Research Institute, FERM BP 283).

18. An *Escherichia coli* transformed with the plasmid of claim 12.

19. An *Escherichia coli* transformed strain of claim 18, which is E15/pAHPCT38 (FERM BP-283).

* * * * *